(12) United States Patent
Kawaguchi

(10) Patent No.: US 9,808,463 B1
(45) Date of Patent: Nov. 7, 2017

(54) SAFE-DRIVING SUPPORT SYSTEM

(71) Applicant: ZaaZ, Inc., Tokyo (JP)

(72) Inventor: Kentaro Kawaguchi, Tokyo (JP)

(73) Assignee: Zaaz, Inc., Tokyo (JP)

( * ) Notice: Subject to any disclaimer, the term of this patent is extended or adjusted under 35 U.S.C. 154(b) by 0 days.

(21) Appl. No.: 15/351,287

(22) Filed: Nov. 14, 2016

(30) Foreign Application Priority Data

Jun. 28, 2016 (JP) ................................ 2016-128100

(51) Int. Cl.
| | |
|---|---|
| *G05D 3/10* | (2006.01) |
| *G05D 3/20* | (2006.01) |
| *A61K 31/522* | (2006.01) |
| *B05B 9/01* | (2006.01) |
| *B05B 12/02* | (2006.01) |
| *A61M 21/00* | (2006.01) |
| *G01C 21/34* | (2006.01) |
| *G01C 21/30* | (2006.01) |
| *G01S 19/45* | (2010.01) |

(52) U.S. Cl.
CPC .......... *A61K 31/522* (2013.01); *A61M 21/00* (2013.01); *B05B 9/01* (2013.01); *B05B 12/02* (2013.01); *G01C 21/30* (2013.01); *G01C 21/3407* (2013.01); *G01S 19/45* (2013.01); *A61M 2021/0077* (2013.01)

(58) Field of Classification Search
USPC ........................ 701/45–46; 600/300; 429/515
See application file for complete search history.

(56) References Cited

U.S. PATENT DOCUMENTS

| | | | | |
|---|---|---|---|---|
| 6,592,245 | B1 * | 7/2003 | Tribelsky ................ | B64F 1/007 362/259 |
| 6,675,081 | B2 * | 1/2004 | Shuman .................. | B60K 28/06 340/436 |
| 7,656,287 | B2 * | 2/2010 | Albert .................. | G06F 19/3418 340/517 |
| 9,302,584 | B2 * | 4/2016 | Walsh .................. | B60K 28/066 |

(Continued)

FOREIGN PATENT DOCUMENTS

| | | | | |
|---|---|---|---|---|
| CN | 104218976 | A  * | 12/2014 | ............... H04B 5/00 |
| CN | 105894733 | A  * | 8/2016 | ......... H04N 5/23229 |

(Continued)

OTHER PUBLICATIONS

Road sign detection on a smartphone for traffic safety; Carrie Pritt; 2014 IEEE Applied Imagery Pattern Recognition Workshop (AIPR); Year: 2014; pp. 1-6, DOI: 10.1109/AIPR.2014.7041927.*

(Continued)

*Primary Examiner* — Cuong H Nguyen

(74) *Attorney, Agent, or Firm* — Rutan & Tucker LLP

(57) ABSTRACT

Providing a system that prevents decrease of attentiveness of drowsiness of a driver of a moving vehicle. A safe-driving support system is provided. The safe-driving support system comprises: a spraying device having a shape being able to be steadily placed near a driving seat of a movable body and spraying in the movable body; a mobile information processing device configured to be able to perform proximity communication with the spraying device and being able to obtain current location information via a GPS; and an information providing server providing the information processing device with information via the Internet.

8 Claims, 8 Drawing Sheets

Diagrammatic perspective view of a spraying device

Explanation figure of a spraying device

(56) References Cited

U.S. PATENT DOCUMENTS

| | | | | |
|---|---|---|---|---|
| 9,604,858 | B2* | 3/2017 | Kamen | C02F 1/041 |
| 2003/0187704 | A1* | 10/2003 | Hashiguchi | G06Q 40/02 |
| | | | | 705/4 |
| 2015/0328985 | A1* | 11/2015 | Kim | H04N 5/23229 |
| | | | | 180/272 |
| 2016/0275801 | A1* | 9/2016 | Kopardekar | G08G 5/0043 |
| 2017/0039045 | A1* | 2/2017 | Abrahami | G06F 8/41 |

FOREIGN PATENT DOCUMENTS

| | | | |
|---|---|---|---|
| JP | H1-221313 | 4/1989 | |
| JP | H6-93286 | 5/1994 | |
| JP | 2003-315080 | 6/2003 | |
| KR | EP 2952403 A3 * | 2/2016 | H04N 5/23229 |
| SG | WO 2006137809 A1 * | 12/2006 | B60R 25/04 |
| WO | 2011/138855 | 11/2011 | |

OTHER PUBLICATIONS

Design and Implement Augmented Reality for Supporting Driving Visual Guidance; Jyh-Horng Lin; Cheng-Min Lin; Chyi-Ren Dow; Cheng-Qian Wang; 2011 Second International Conference on Innovations in Bio-inspired Computing and Applications Year: 2011; pp. 316-319, DOI: 10.1109/IBICA.2011.84.*

Research on the anti-collision system of surface coal mine based on the highly accurate GPS location technology; Wei Wang; Runjing Zhou; 2009 9th International Conference on Electronic Measurement & Instruments; Year: 2009; pp. 3-196-3-199, DOI: 10.1109/ICEMI.2009.5274323.*

Intelligent Car Control and Recognition Embedded System; Vilem Srovnal; Zdenek Machacek; Radim Hercik; Roman Slaby; Vilem Srovnal; Proceedings of the International Multiconference on Computer Science and Information Technology; Year: 2010; pp. 831-836, DOI: 10.1109/IMCSIT.2010.5679932.*

Markov Random Field model for single image defogging; Laurent Caraffa; Jean-Philippe Tarel; 2013 IEEE Intelligent Vehicles Symposium (IV); Year: 2013; pp. 994-999, DOI: 10.1109/IVS.2013.6629596.*

Using Smartphones in Healthcare and to Save Lives; Gabor Kiss; 2011 International Conference on Internet of Things and 4th International Conference on Cyber, Physical and Social Computing; Year: 2011; pp. 614-619, DOI: 10.1109/iThings/CPSCom. 2011. 90.*

Experimental study on the effects of ambient pressure conditions on spray characteristics of water mist; Changfa Tao; Xin Cai; Xinshi Wang; 2011 Second International Conference on Mechanic Automation and Control Engineering; Year: 2011; pp. 7363-7366, DOI: 10.1109/MACE.2011.5988751.*

An Eyes-Free In-car User Interface Interaction Style Based on Visual and Textual Mnemonics, Chording and Speech; Frode Eika Sandnes; Yo-Ping Huang; Yeh-Min Huang; 2008 International Conference on Multimedia and Ubiquitous Engineering (mue 2008); Year: 2008; pp. 342-347, DOI: 10.1109/MUE.2008.50.*

Publication on the applicant's Facebook page, Publication Date: Jun. 1, 2016, 2 pages, Publisher: ZaaZ inc.

Presentation materials to potential investers at public space, Publication Date: Jun. 1, 2016, 13 pages, Mr. Kentaro Kawaguchi, the president of the Applicant and inventor of the application.

* cited by examiner

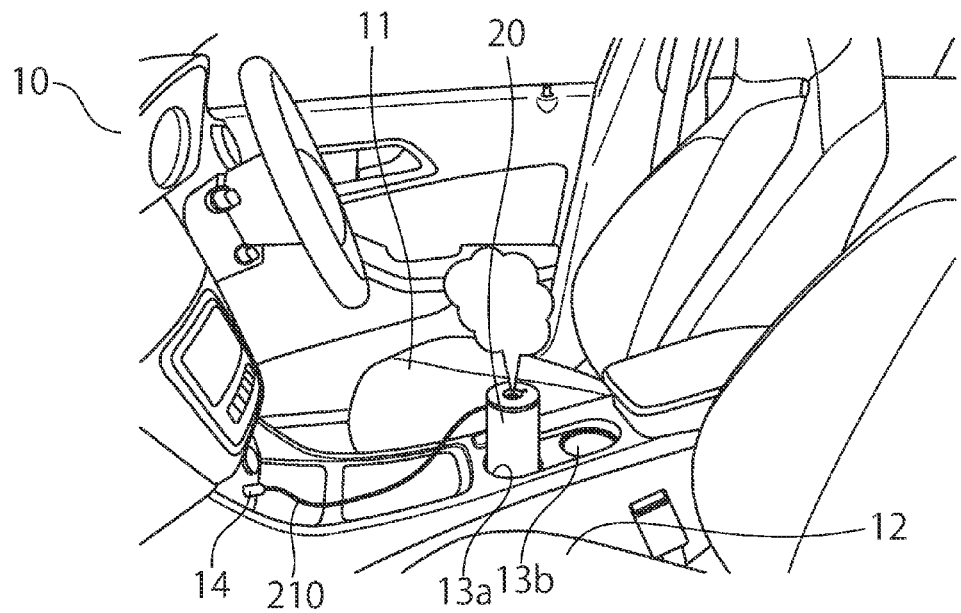
Fig. 1(a) Example of placement of a spraying device
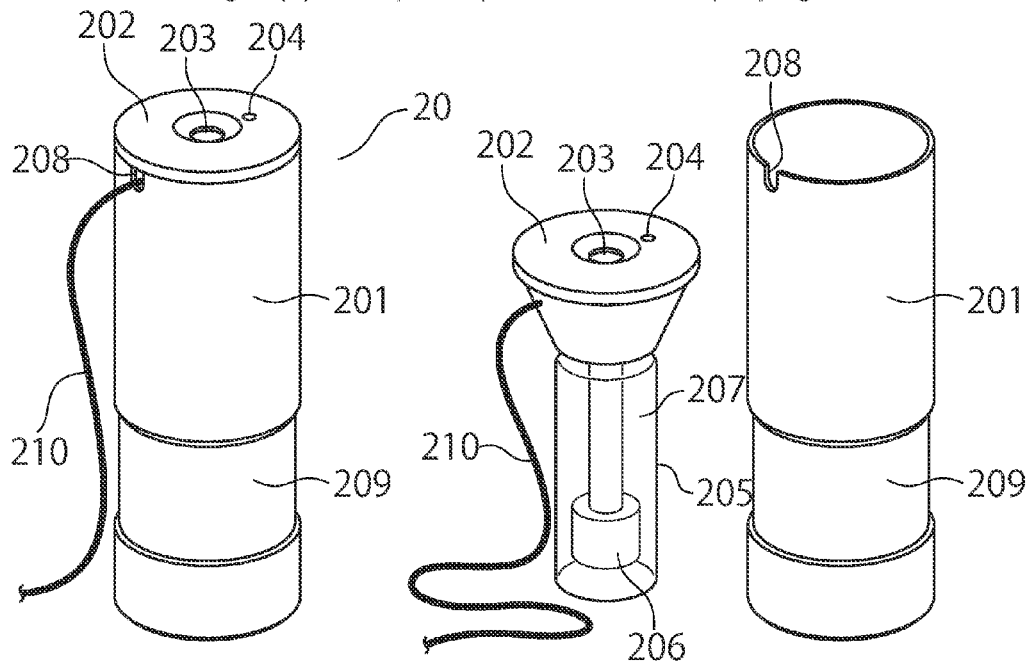
Fig. 1(b) Diagrammatic perspective view of a spraying device
Fig. 1(c) Partially exploded view of a spraying device
Explanation figure of a spraying device

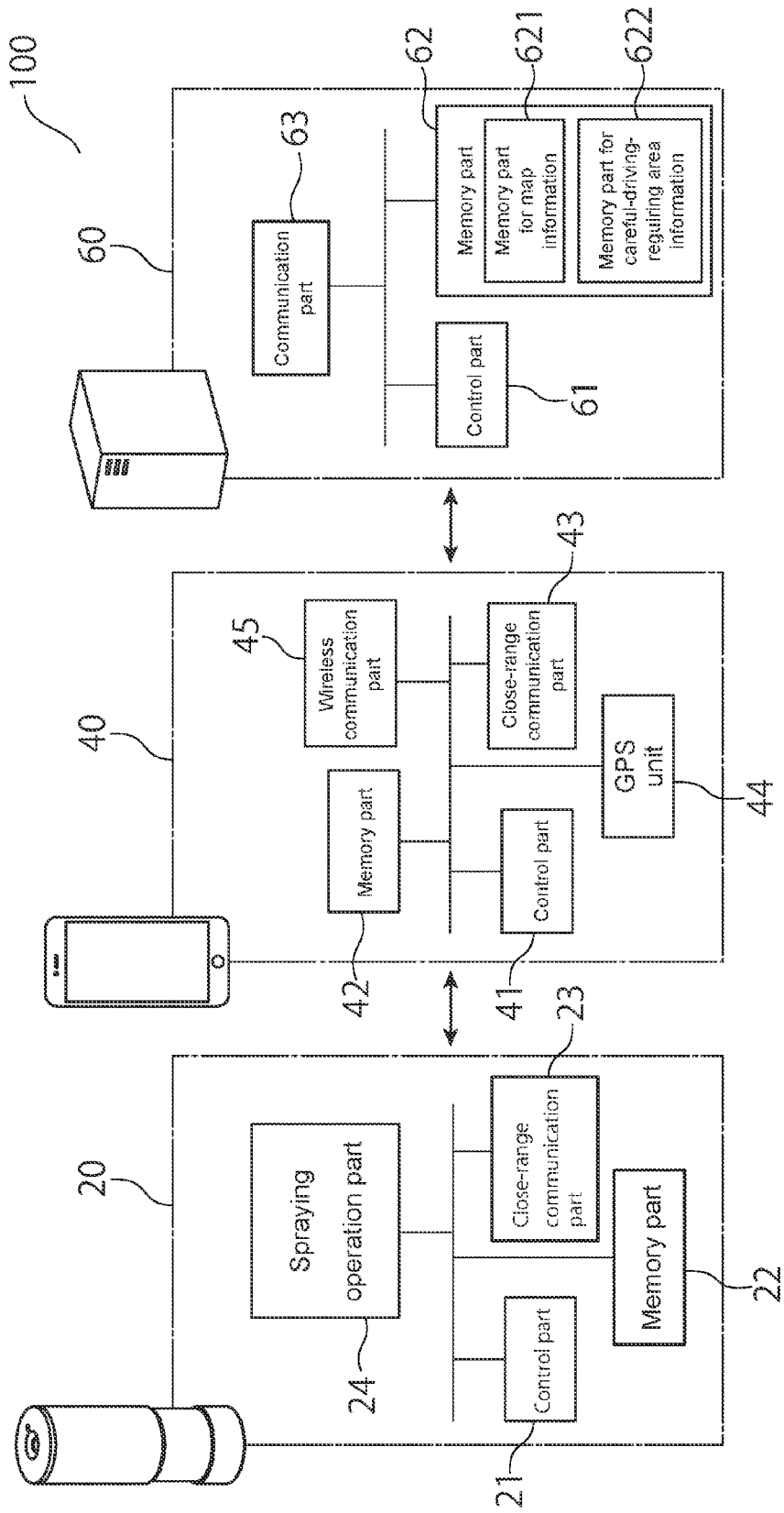
[Fig.2]
Configuration diagram for a main part of a system

[Fig.3]
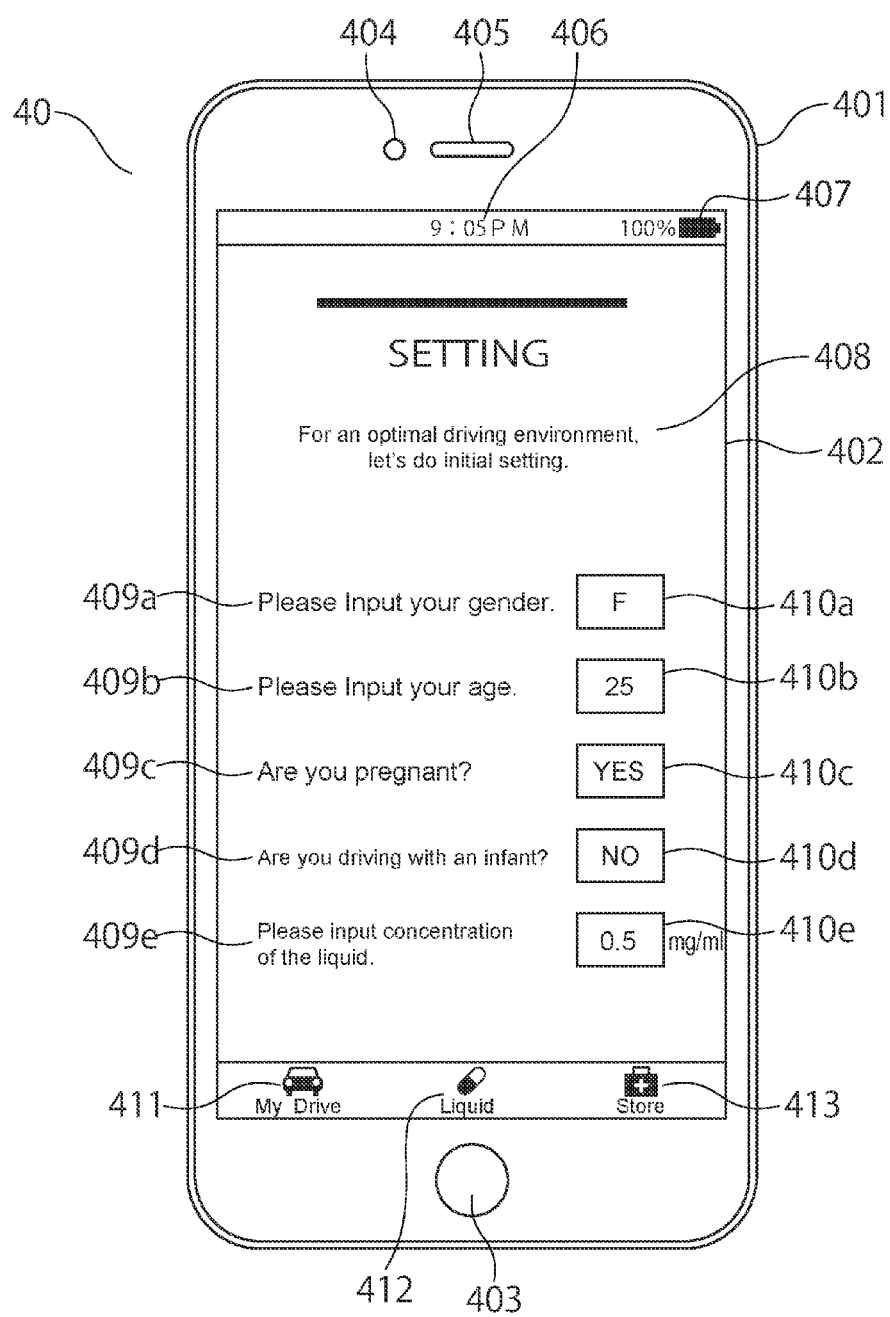
Explanation figure for showing an image displaying example at initial setting

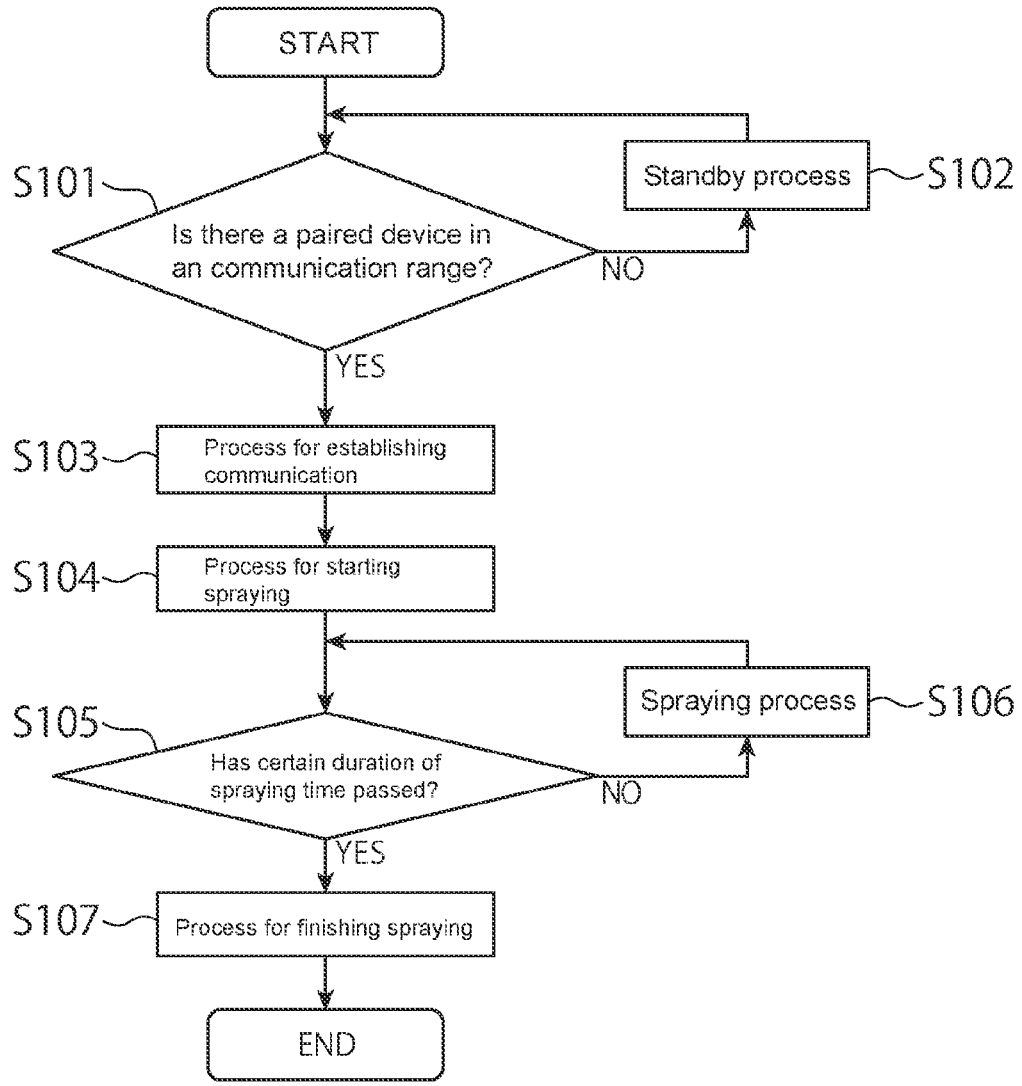
Flow chart regarding operation of a spraying device when a user gets in a car
[Fig.4]

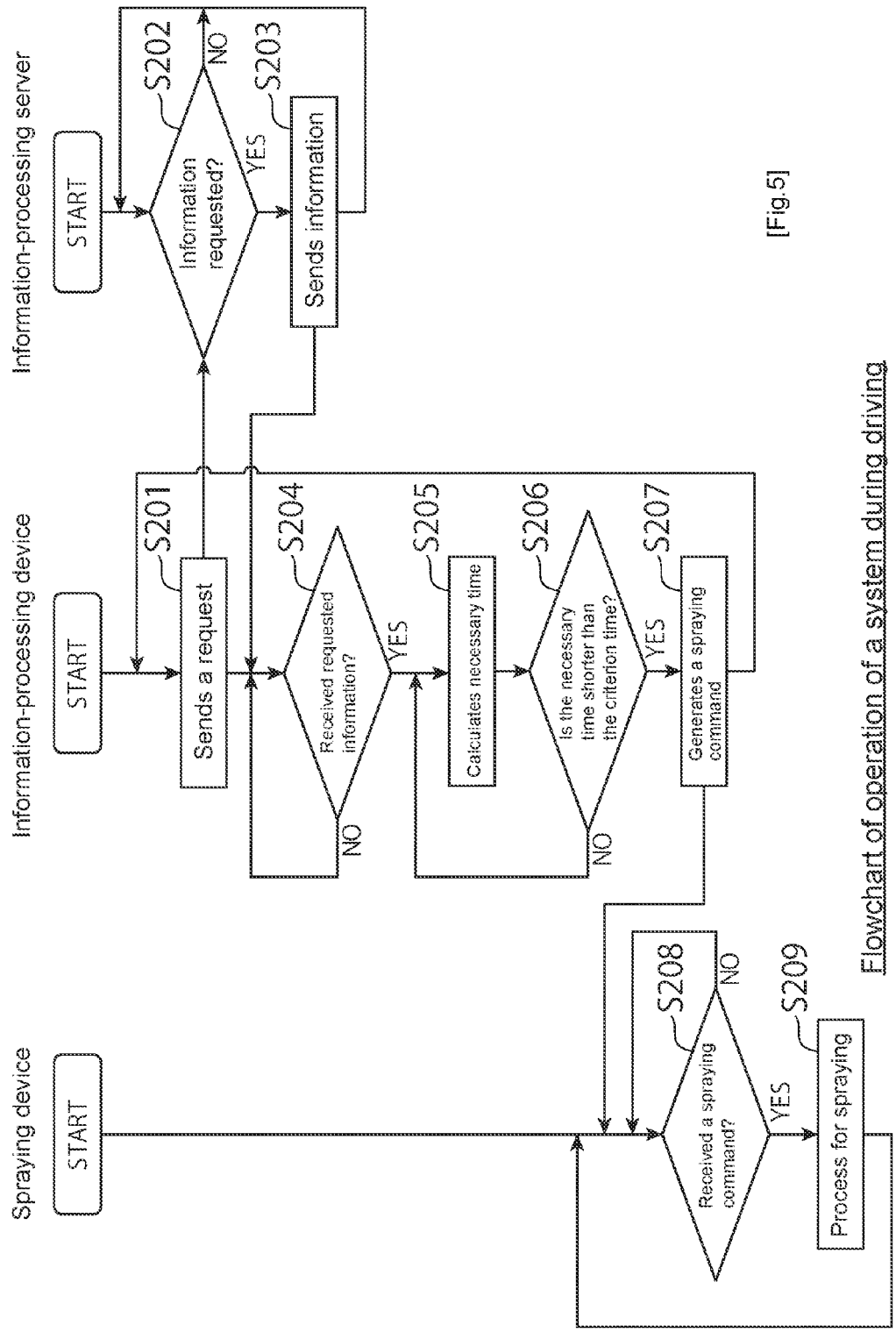
[Fig. 5]
Flowchart of operation of a system during driving

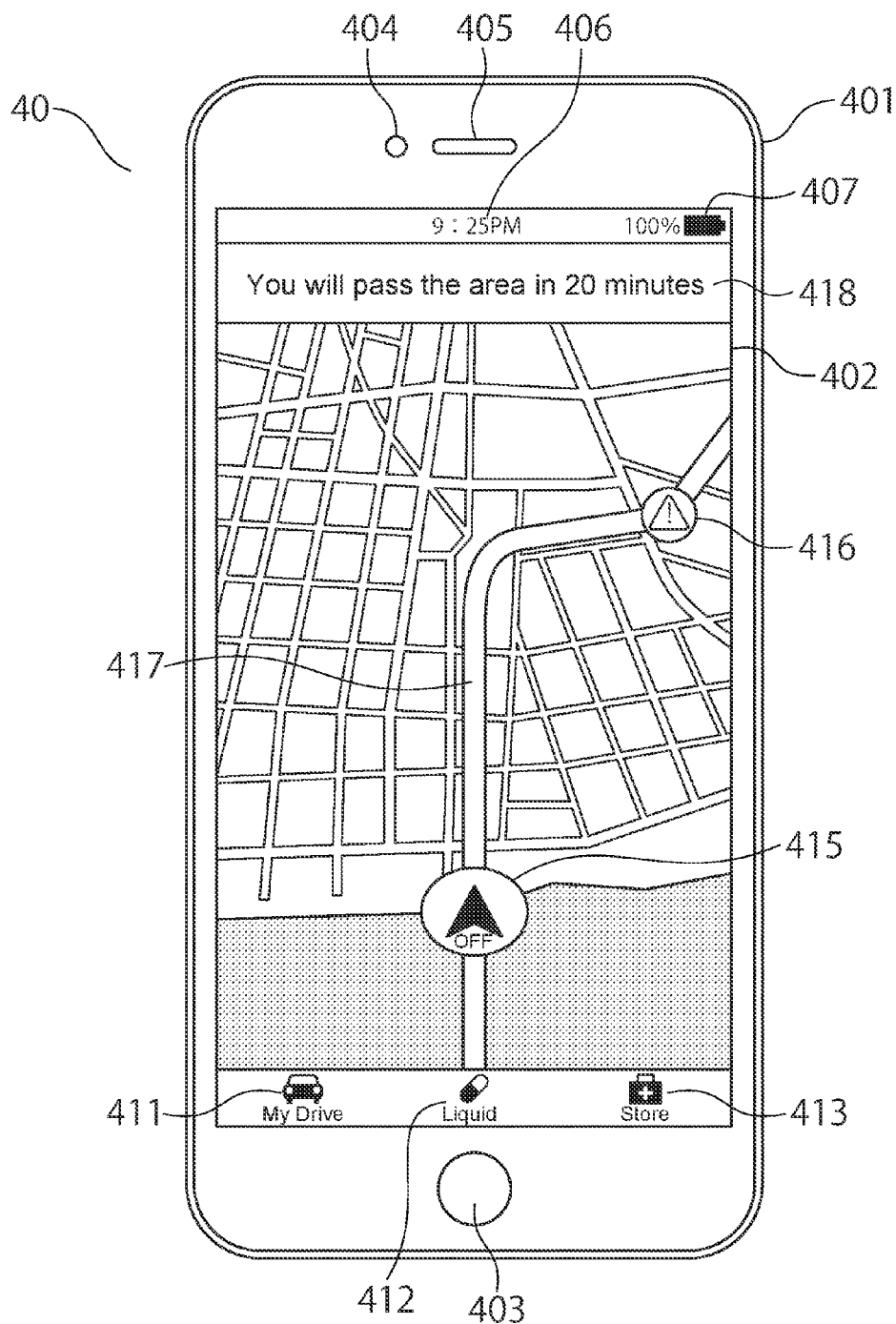
Explanation figure for showing an image displaying example during driving
[Fig.6]

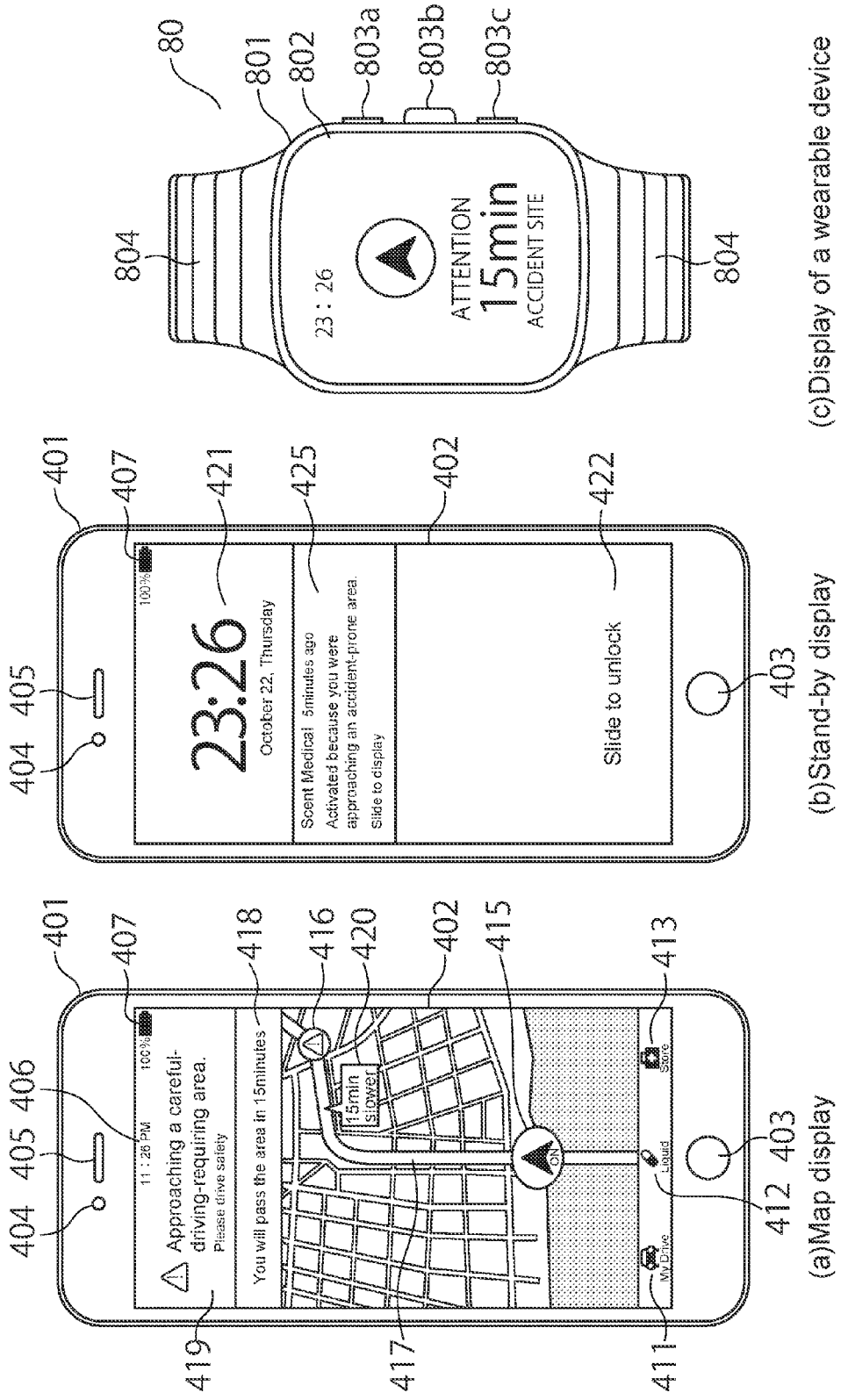

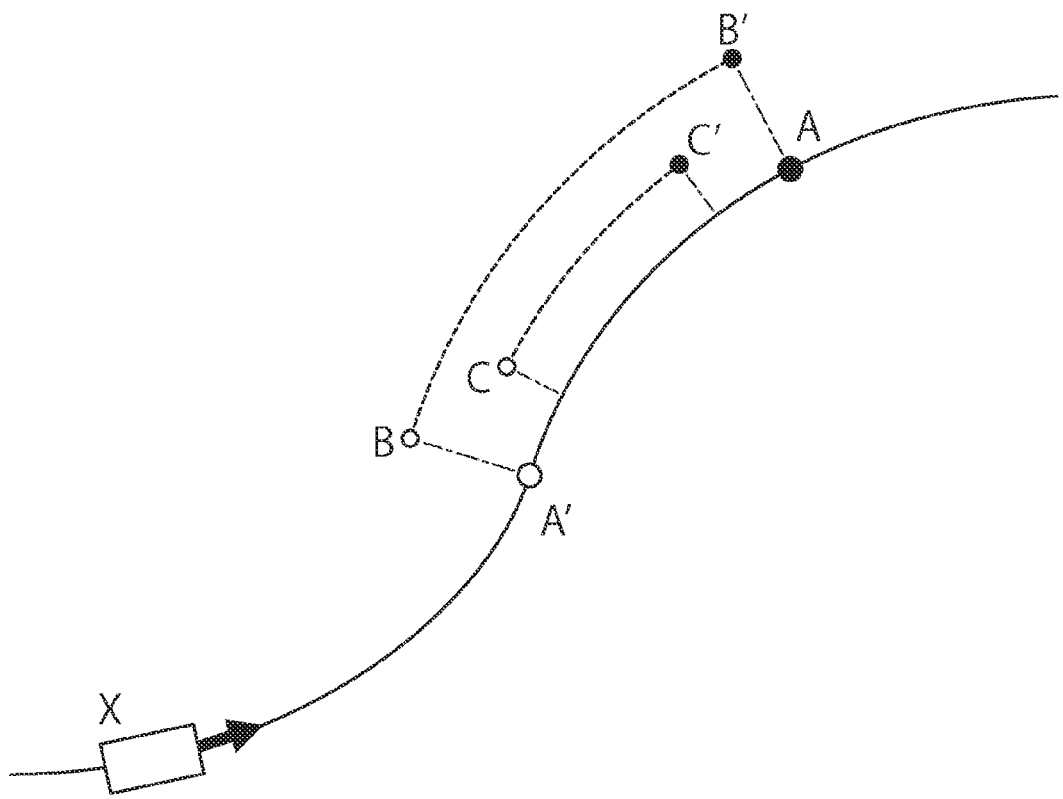
Explanation figure regarding a variation of spraying
[Fig.8]

SAFE-DRIVING SUPPORT SYSTEM

RELATED APPLICATIONS

This application is related to and claims the benefit under 35 USC §119 of Japanese Application JP 2016-128100 titled "Safe-Driving Support System" filed Jun. 28, 2016, which is incorporated herein by reference it its entirety.

TECHNICAL FIELD

The present invention is relevant to a system that supports safe driving of moving vehicles, including cars.

BACKGROUND OF THE INVENTION

A driver of moving vehicles, including cars, trains, planes and ships, sometimes feels drowsy during the drive. This drowsiness decreases attentiveness of the driver, leading to various accidents. To prevent this kind of drowsiness and its consecutive decrease of attentiveness, various methods have been developed. One of the most common methods is letting the driver inhale gas or liquid containing awakening substance, for it is expected to intercept driving maneuver less.

One of the typical methods to let the driver inhale awakening gas or such liquid is to place an aroma diffuser of which aroma contains incense and caffeine, which has direct-awakening substance, to let it evaporate. This provides an awakening environment or a preventive environment of drowsiness (Patent literature 1).

PRIOR ART DOCUMENT

Patent Literature

[Patent literature 1] Japanese Unexamined Patent Application Publication No. 116-93286

DESCRIPTION OF THE PRESENT INVENTION

Technical Problem

However, when the aroma chemical, which contains caffeine, evaporates, the evaporation is under no control. This lets it keep on evaporating in a vehicle and has a problem that the vehicle is full of the aroma even when it should not (e.g., when the driver tries to pull over the car and take a nap). Additionally, the evaporation goes on even when it is unnecessary, leading to waste of the aroma chemical.

The present invention is developed to solve the problem described above. The purpose is to provide a method to prevent decrease of a driver's attentiveness because of drowsiness during driving a vehicle, including cars.

Additional purposes and effects of the present invention will be quite understandable for those in the art through the following description.

Method to Solve the Problem

The technical problem described above is solved by the following components.

A safe-driving support system comprises:

a spraying device having a shape being able to be steadily placed near a driving seat of a movable body and spraying in the movable body;

a mobile information processing device configured to be able to perform proximity communication with the spraying device and being able to obtain current location information via a GPS; and an information providing server providing the information processing device with information via the Internet; and the spraying device, further comprising:

a liquid container containing water solution containing caffeine;

a spraying operation part spraying water solution containing caffeine contained in the liquid container; and wherein the spraying device is configured to spray in the movable body by activating the spraying operation part in response to a spraying command from the information processing device that established proximity communication; and the information providing server, further comprising:

a map information memory part memorizing map information;

attention requiring area memory part memorizing attention requiring area information showing areas requiring careful driving; and wherein the information providing server is configured to send the map information and the attention requiring area information, respectively, to the information processing device in response to a request from the information processing device; and wherein the information processing device obtains the map information and the attention requiring area information from the information providing server by requesting to the information providing server, calculates necessary time to the attention requiring area based upon the map information and the attention requiring area information obtained from the information providing service and the current location information, and generates a spraying command to the spraying device if it is judged that the necessary time is shorter than a criterion time; and wherein the spraying device activates the spraying operation part based upon the spraying command and sprays the water solution containing caffeine in the movable body.

This framework surely increases attentiveness of the driver or prevents decrease of attentiveness of the driver in the careful-driving-requiring area where the driver should drive carefully, leading to achieving support of safe driving.

Additionally, the above safe-driving support system may further comprises a watch-shaped wearable device being able to perform proximity communication with the information processing device and having a display, and wherein an image showing spraying may be displayed on the display of the wearable device if the information processing device generates the spraying command to the spraying device.

This framework enables the display of the wearable device to show whether the system has sprayed. This hardly distracts the driver from the front view when confirming whether the system is working or not.

Additionally, in the above safe-driving support system, the proximity communication between the spraying device and the information processing device may require a paring process as an initial setting; once the paring process is performed, the proximity communication may be automatically established when the spraying device and the information processing device are in a communicable range; and the spraying device may spray immediately after the automatic establishment.

This framework enables the user to inhale the water solution containing caffeine right after getting in the car. The user can enjoy the awakening effect or the preventive effect of drowsiness. This contributes to safe driving.

Additionally, in the above safe-driving support system, the information processing device may be configured to obtain configuration information including attribute information of a user or his or her company, and the spraying device may control spraying water solution containing caffeine according to the configuration information.

This framework enables the support system not to spray the water solution containing caffeine toward users or his/her company for who caffeine may do harm. This achieves the healthy and user-friendly safe-driving support system even for such users or company.

Also, in the above safe-driving support system, the information providing server further comprises:

a route searching part to search the shortest distance route or the shortest time route between a current location relating to current location information and a destination relating to destination information when the current information and the destination information are provided from the information processing device, and to provide the information processing device with route information relating to the shortest distance route or the shortest time route, and wherein the information providing server may provide the information processing device with attention requiring area information on the shortest distance route or the shortest time route, wherein the information processing device may provide a navigation function based upon the map information and the route information obtained from the information providing server and the current location information, and calculate necessary time to the attention requiring area on the shortest distance route or the shortest time route based upon the map information and the route information obtained from the information providing server, the attention requiring area information on the shortest distance route or the shortest time route and the current location information.

This framework enables the user to inhale caffeine-containing water solution 207, which has the awakening effect or the preventive effect of drowsiness, before criterion time to get to the careful-driving-requiring area in the course to the destination, leading to safe driving. The fixed route saves the number of times of evaporation and thus prevents waste of the caffeine-containing water solution.

Additionally, in the above safe-driving support system, the configuration information further comprises concentration information of the water solution containing caffeine, and wherein the denser the concentration of the water solution containing caffeine becomes, the shorter the spraying time of the water solution containing caffeine becomes.

This framework saves the caffeine-containing water solution, since the system does not spray it more than needed when using highly-caffeine-concentrated water solution, which is more effective as awakening substance or preventive substance of drowsiness.

Additionally, in the above safe-driving support system, the information processing device may accumulate spraying amount of the water solution containing caffeine every time the information processing device generates the spraying command, and when the total amount of sprayed water solution containing caffeine calculated based upon the accumulation result and the concentration information is greater than a prescribed value according to the configuration information, the information processing device may stop spraying the water solution containing caffeine.

This framework achieves both prevention of drowsiness by spraying of the spraying device and prevention of overdose of caffeine.

Additionally, in the above safe-driving support system, the water solution containing caffeine may be odorless.

This framework enables spray of liquid that has the awakening effect or the prevention effect of drowsiness regardless of personal preference of the user.

Effect of the Invention

The present invention definitely enhances attentiveness of a driver or prevents decrease of attentiveness in a careful-driving-requiring area where the driver should drive more carefully, and this contributes to achievement of support for safe driving.

BRIEF DESCRIPTION OF DRAWINGS

FIG. 1(*a*) is an explanation figure of a spraying device; an example of placement of a spraying device.

FIG. 1(*b*) is an explanation figure of a spraying device; a diagrammatic perspective view of a spraying device.

FIG. 1(*c*) is an explanation figure of a spraying device; a partially exploded view of a spraying device.

FIG. 2 is a configuration diagram for a main part of a system.

FIG. 3 is an explanation figure for showing an image displaying example at initial setting.

FIG. 4 is a flow chart regarding operation of a spraying device when a user gets in a vehicle.

FIG. 5 is a flowchart of operation of a system during driving.

FIG. 6 is an explanation figure for showing an image displaying example during driving.

FIG. 7 is an explanation figure for showing an image displaying example when spraying.

FIG. 8 is an explanation figure regarding a variation of spraying.

DESCRIPTION OF EMBODIMENT

The following description is about an example of embodiment of the support system for safe driving enabled by the present invention with using figures on the attachment as reference.

1. First Embodiment 1.1 Structure of Hardware
1.1.1 Structure of a Spraying Device FIG. 1 (*a*) shows an example of placement of a spraying device 20 in a car. In the figure, between a driving seat 11 and a passenger seat 12 are two drink holders in the shape of horizontally-cut tube 13*a* and 13*b*. The cylinder-shaped spraying device 20 is inserted in the 13*a* to be stable during drive. The spraying device 20 is connected to a plug 14 for a cigarette socket via a power-supply code 210 to obtain power to operate.

Incidentally, this embodiment includes a structure where the plug 14 and the power supply-code 210 are directly connected, yet the way of connection does not have to be always identical to this. For example, it is possible to have connecting a user-interface, including USBs, between the plug 14 and the power-supply code 210, to connect the both via the interface. Also, the spraying device 20 may contain a power-supply unit as a battery to remove the power-supply code 210 completely.

Additionally, this embodiment has the spraying device 20 in the drink holder 13*a*. However, the present invention only requires the spraying device 20 to be placed steadily in a car 10 and to let the driver inhale the spray. Thus, the structure above should be just an example, and the spraying device 20 may be placed near a fan of an air conditioner of the car 10 (e.g., fixed to a louver of the air conditioner).

FIG. 1 (*b*) and FIG. 1 (*c*) show a diagrammatic perspective view of the spraying device 20 and a decomposition of the spraying device 20 respectively. Below is detailed description of the hardware structure of the spraying device 20 with using these figures as reference.

It is clear from the FIG. 1 (*b*) that the spraying device 20 has cylinder-shaped appearance and also has a constricted region 209 little below its middle part. This region has smaller diameter. On the top edge of the spraying device 20 is a cut 208 in which the power-supply code 210 runs. The power-supply code 210 is placed via the cut 208. On the top of the spraying device is a body containing a spraying operation part 202. The contained liquid is sprayed from a porous piezoelectric element 203 located at a center of the body containing the spraying operation part 202, as this is mentioned later. During spray, an operation lamp 204 lights blue to indicate the operation.

It is clear that the spraying device 20 is built by inserting aggregation, consisting of the body containing the spraying operation part 202 and a cylinder-shaped liquid container 205, into a midair cylinder part 201 from the top. The body containing the spraying operation part 202 and the liquid container 205 are detachable. Removal of the liquid container 205 enables the user to pour liquid into the liquid container 205.

In this embodiment, the liquid container 205 contains caffeine-containing water solution 207, which contains caffeine and is odorless or scentless. At a center of the liquid container 205 is a wet retainer made from polyester 206 that absorbs and retains the caffeine-containing water solution 207. The wet retainer 206 directly touches the piezoelectric element 203 inside the body containing the spraying operation part 206. Thus, when the piezoelectric element 203 operates and vibrates, the caffeine-containing water solution 207 retained in the retainer 206 is sprayed from the top of the spraying device 20.

This framework enables the spray of the liquid that has the awakening effect or the prevention effect of drowsiness regardless of personal preference of the user, since the caffeine-containing water solution 207 is scentless.

1.1.2 Structure of the System

The following description is the structure of a main part of the safe-driving support system 100 that contains the spraying device 20. The safe-driving support system 100 is configured by communication between the spraying device 20 and information-processing device 40, and between the information-processing device 40 and information-providing server 60.

The spraying device 20 comprises a control part 21 for such as CPU, a memory part 22 for such as a memory, a close-range communicator 23, which utilizes Bluetooth (registered trademark), and a spraying operation part 24 that operates the piezoelectric element 203. All of these are connected via bus. The spraying device 20 is connected to the information-processing device 40 via the close-range communicator 23 to operate in accordance with a command from the information-processing device 40.

The information-processing device 40 comprises: a control part 41 for such as a CPU that performs various application programs; a memory part 42 for such as a memory that stores data including application programs setting information; a close-range communicator 43 that communicates with the close-range communicator 23 of the spraying device 20 in a close range; a GPS unit 44 that retrieves the current location of the information-processing device 40 with GPS (Global Positioning System); and a wireless communicator 45 for wireless connection to the Internet. All of these are connected via bus. The information-processing device 40 may be a mobile information-processing device, including a smartphone, a tablet, and a wearable device. An application program to control the operation of the spraying device 20 is stored in the memory part 42 of the information-processing device 40. When the control part 21 performs application programs, the following various operations are achieved. Incidentally, the information-processing device 40 is connected to the information-providing server 60 via the Internet.

The information-providing server 60 comprises: a control part 61 for such as CPUs; a memory part 62 for such as memory and storage; and a communicator 63 for connection to the Internet. All of these are connected via bus. Additionally, the memory part 62 comprises: a map-data memory part 621 that contains map data; and a careful-driving-requiring-area information memory part 622 that contains careful-driving-requiring-area information, which indicates an area where the user should drive more carefully. Incidentally, the memory part 62 can be placed outside of the information-providing server 60 independently.

The area where the user should drive more carefully means an area or a location where the driver should be more careful than usual (e.g., a an accident-prone area where the user should be careful or a trafficy area where the driver easily feels drowsy and hits another car).

Incidentally, the composition described in FIG. 2 is only a main part. Thus, the composition may contain something not described in FIG. 2, such as a power-supply unit.

1.2 Operation

The following description is the operation of: the spraying device 20; the information-processing device 40; the information-providing server 60 when the application program that controls the spraying operation of the spraying device 20 is performed; and the safe-driving support system 100 including these operations.

1.2.1 Initial Setting Operation

Prior to performing the application program that controls the spraying device 20, a user pairs the information-processing device 40 with the spraying device 20 via such as Bluetooth (registered trademark). This pairing enables automatic establishment of proximity communication between the spraying device 20 and the information-processing device 40 if the two devices are sufficiently close to each other.

Following this, when the information-processing device 40 performs the application program that controls the spraying device 20, the initial setting screen appears on a display 402, which is of the information-processing device 40, as described in FIG. 3.

It is clear from FIG. 3 that the information-processing device 40 comprises: a body 401; a display 402 that is used for touch input at a center of the body 401; an operation button 403 to control the information-processing device 40; an in-camera 404 that takes an image of a figure facing the display 402; and a speaker 405 that outputs voices including that of calls. On the top of the display 402 are: a time indicator 406 that shows the time; and a power indicator 407 that shows the remaining power of the information-processing device. Plus, at a middle-upper part of the initial setting screen is a message display 408 saying, "For an optimal driving environment, let's do some initial setting." After reading the message 408, the user sees several setting items 409 aligned in a line vertically below the message display 408 and enters information to a setting field 410 accordingly. At the bottom of the display 402 are 3 mode-selection buttons consisting of: "Mydrive" mode selection button 411; "Liquid" mode selection button 412; and "Store" mode selection button 413. All of these modes are selectable by touch.

The user inputs necessary information to the setting field 410 while seeing the setting items 409, relevant to the attribute information (including the age of the user and the gender of the user) and the caffeine concentration of the caffeine-containing water solution 207. First, the user inputs his/her sex to a setting field 410a after seeing the first setting item 409a, "Please input your sex". The example in FIG. 3 has selected Female. Next, the user inputs his/her age by digit to a setting field 410b after seeing the second setting item 409b, "Please input your age". The example in FIG. 3 has entered 25 years old. Following this, the user inputs information about her pregnancy to the third setting field 410c after seeing the third setting item 409c, "Are you pregnant?" The example in FIG. 3 has selected "YES". Incidentally, the third setting item 409c and the third setting field 410c may only appear if the user selects Female at the first setting field 410a. Then, the user inputs whether or not his/her company includes a baby to the 4th setting field 410d after seeing the setting item 409d, "Are you driving with an infant?" The example in FIG. 3 has selected "NO", which means that she drives with no baby in the car. Finally, the user inputs caffeine concentration of the caffeine-containing water solution 207 used by the spraying device 20 to the 5th setting field 410e after seeing the 5th setting item 409e, "Please input the concentration of the liquid". The example in FIG. 3 has entered 0.5 mg/ml as the concentration of the liquid. As described above, the user completes the initial set-ups. Incidentally, the inputted data here are stored in the memory part 42 as attribute information or concentration information, and are used for various operations, which are described later.

Incidentally, "Mydrive" mode is a mode where the current location of the information-processing device 40 on the map appears on the display 402, according to the current location data retrieved by a GPS unit 44 of the information-processing device 40 and the map data provided by the information-providing server 60. In "Liquid" mode, the detail of the currently used water solution, which is contained in the spraying device 20, is displayed. "Store" mode enables the user to purchase another liquid by connecting to an online store via the Internet.

1.2.2 Operation when Riding

The following description is about operation when the user with the mobile information-processing device 40 gets in the car 10 in which the spraying device 20 is placed, with reference of FIG. 4.

The spraying device 20 that is paired with the information-processing device 40 always checks whether the information-processing device 40 is in its communication area or not, which check is called S101. If the information-processing device 40 is not in the communication area, which situation is called S101NO, the spraying device 20 performs stand-by process, which is called S102, and re-checks whether the information-processing device 40 is in the communication area. When the user who is wearing the mobile information-processing device is close to the car 10, in which the spraying device 20 is placed, the spraying device 20 detects availability of the information-processing device 40 in the communication area. This situation of availability of the information-processing device 40 is called S102YES. Then, the spraying device 20 tries to establish the communication, which establishment is called S103. After completion of the establishment of the communication, the control part 21 of the spraying device 20 gives a command to the spraying operation part 24 to start spraying water solution and performs spray-start operation, which is called S104. This makes the spraying operation 24 operates and the caffeine-containing water solution 207 is sprayed from the piezoelectric element 203. Then, for certain duration of spraying, the spraying operation by the spraying operation part 24 continues, which is called S102. After the certain duration, a spray-stop process is performed to stop spraying, which is called S107. Here, the time within the certain duration is called S105NO and completion of the certain duration is called S105 YES.

This framework sprays the caffeine-containing water solution 207 in the car when the user who is wearing the information-processing device 40 is close to the car 10 to get in the car 10. This enables the user to inhale the caffeine-containing water solution 207 right after getting in the car 10 and therefore enjoy the awakening effect or the preventive effect of drowsiness shortly after starting driving, which contributes to safe driving.

1.2.3 Operation During Driving

The following description is operation of the safe-driving support system 100 when the user is driving the car 10, with reference of FIG. 5, FIG. 6 and FIG. 7. Here, the information-processing device 40 is configured to "My drive" mode, which is described above.

In the default, the spraying device 20 is in stand-by mode until it receives a spraying-command, which state is called S208NO, and the information-providing server 60 is in stand-by mode until it receives a request of information, which state is called S202NO.

In this state, when the information-processing device 40 starts a process, the information-processing device 40 sends to the information-providing server 60: the current location information of the information-processing device 40, which is retrieved from the GPS unit 44; and a request of information, which operation is called 5201. Then, the information-processing device 40 stands ready until it receives the requested information from the information-providing server 60, which state is called S204NO.

When the information-providing server 60 receives a request of the current location information and other information, which situation is called S202YES, the information-providing server 60 sends to the information-processing device 40: the map data around the current location, which is retrieved from the map-data memory part 621; and careful-driving-requiring-area information, which is about accident-prone areas or traffic jams where the user should drive more carefully, which operation is called S203.

When the information-processing device 40 receives the map data around the current location and careful-driving-requiring-area information, which state is called S204YES, the information-processing device 40 starts to calculate the necessary time to the nearest careful-driving-requiring area in the course to his/her destination, which calculation is called S205. In detail, the information-processing device 40 calculates the distance between the current location and the nearest careful-driving-requiring area, in a basis of: the current location information; the map data; and the careful-driving-requiring-area information. Additionally, the information-processing device 40 calculates the average velocity of the information-processing device 40 and the direction that the information-processing device 40 faces, which are namely both of the velocity and the direction of the car 10, in a basis of a history record of the current location information. Following this, the information-processing device 40 calculates the necessary time to get to the careful-driving-requiring area from the current location, in a basis of the distance between the current location and the careful-driving-requiring area and the average velocity. The necessary time calculated appears on the display 402, which is mentioned later again. The process described above is repeated until the necessary time calculated has become shorter than a certain criterion time, which is 15 minutes in this embodiment. This state where the necessary time is longer than the criterion time is called S206NO. This means, the information-processing device 40 repeats the process described above until the necessary time to get to the nearest careful-driving-requiring area in the heading direction has become 15 minutes or shorter. The method to calculate the necessary time to get to the careful-driving-requiring area may be different one, including many common methods. In this embodiment, the information-processing device 40 does the calculation, but the information-providing server 60 may do the same job instead.

FIG. 6 shows an example of display on the screen of the display 402 of the information-processing device 40 when the necessary time to get to the nearest careful-driving-requiring area is 20 minutes, which means the necessary time is longer than the criterion time (15 minutes). In the figure, identical components to those of FIG. 3 have identical signs.

In a middle of the display 402 is a map of the area around the current location based on the obtained map data, and under the middle part is a circle-shaped indicator 415 that indicates the current location on a way 417, where the car is currently moving. Inside the location indicator 415 are: an arrow that indicates the heading direction; and an "OFF" that indicates that the spraying device 20 is not spraying now. This framework enables the user to know his/her current location and his/her heading direction on a map by the map around the area of his/her current location and the location indicator 415. Additionally, the user can ensure that water solution is not being sprayed by the OFF, which is inside the location indicator 415.

At an upper part of the display 402 is a necessary-time-displaying region 418 that shows the necessary time calculated with the message, "Passing in 20 minutes". Additionally, the spot, in the way 417, where the information-processing device 40 is going to pass, has an exclamation-mark warning sign 416 that indicates the spot is the careful-driving-requiring area where the user should drive more carefully. This framework enables the user to know the user is going to pass through the careful-driving-requiring area, where the user should drive more carefully, in 20 minutes.

Back to FIG. 5, when the necessary time calculated is equal to or shorter than the criterion time, which is 15 minutes in this embodiment, the information-processing device 40 gives a spraying-command that may include duration of spraying to the spraying device 20. The state where the necessary time calculated is equal to or shorter than the criterion time is called S206YES and the following command is called 5207. Upon receiving the spraying-command, which reception is called S208YES, the spraying device 20 operates the piezoelectric element 203 via the spraying operation part 24 upon the spraying-command, and sprays the caffeine-containing water solution 207 for certain duration, which spraying is called S209. This means that the spraying device 20 sprays the caffeine-containing water solution 207 when the necessary time to get to the careful-driving-requiring area is 15 minutes or shorter. The duration of spraying of the spraying device 20 is customizable. This may be 10 minutes or so.

FIG. 7 shows an example of displayed screens of devices when the spraying device 20 is spraying water solution. In the figure, identical components to those of FIG. 3 have identical signs.

FIG. 7 (*a*) shows an example of a displayed screen on the display 402 of the information-processing device 40 when the necessary time to get to the careful-driving-requiring area is 15 minutes. It is clear from FIG. 7 (*a*) that on the display 402 is a caution-displaying region 419 to remind the user of carefulness with a message, "Approaching a careful-driving-requiring area. Please drive safely", above the necessary-time-displaying region 418, in addition to the display in FIG. 6. Additionally, on the currently-driving way 417 is a speed-reminder 420 that indicates that the driver should drive slow in 15 minutes by "15 min slower". Inside the current location indicator 415 is "ON" that indicates that the spraying device 20 is spraying water solution now. This framework enables the user to know that the user is going to get to the careful-driving-requiring area in 15 minutes and that the spraying device 20 is spraying water solution.

Spraying of the spraying device 20 is also ensured when the information-processing device 40 is in stand-by mode. FIG. 7 (*b*) shows an example of screen display on the display 402 when the information-processing device 40 is in stand-by mode. In this mode, at an upper part of the display 402 is a time-displaying region 421 that shows the date and the time, and at a bottom part of the display 402 is a slide-lock displaying region 422 that is unlocked by a slide. Below the time-displaying region 421 is an information notice region 425 that shows a message, "Scent Medical 5 minutes ago. Activated because you were approaching an accident-prone area. Slide to display". This display shows that an application program named "Scent Medical" has been performed in the background and notifies that the information-processing device 40 sprayed water solution 5 minutes ago because it approached an accident-prone area or that it has begun to spray water solution. This framework enables the user to check whether the spraying is done or not even if the scentless caffeine-containing water solution 207 is sprayed.

Additionally, the information-processing device 40 may be connected to a watch-shaped wearable device 80, which the user can put on his/her wrist, via such as Bluetooth (registered trademark). Here, when the spraying device 20 sprays water solution, the wearable device 80 receives a certain notice via the information-processing device 40.

FIG. 7 (*c*) shows an example of screen display of the wearable device 80 when the spraying is performed. The wearable device 80 comprises a main part 801 and a band 804. The main part 801 comprises a displaying part 802 and various buttons whose signs are 803*a*, 803*b*, and 803*c* here. The displaying part 802 displays a message, "ATTENTION 15 min ACCIDENT SITE". This message indicates that the driver gets to the accident-prone area and that the spraying device 20 has sprayed water solution.

This framework enables the user to check surely whether the spraying is done or not even if the caffeine-containing water solution 207 is sprayed. The watch-shaped wearable device 80 enables the user to check whether the spraying is done or not near the steering wheel. This hardly distracts the user from the front view to check whether the spraying is done or not Additionally, the driver can inhale the caffeine-containing water solution 207 sufficiently before getting to the careful-driving-requiring area, and this surely contributes to drowsy-less driving in the careful-driving-requiring area, including an accident-prone area. This enables the user to drive safe. This framework is based on a finding of the inventor that it takes time for the driver to enjoy the awakening effect or the preventive effect of drowsiness after inhaling the caffeine-containing water solution 207.

2. Variations 2.1 Co-Operation with Set Information

In the embodiment above, the spraying is always done when getting in the car or before the criterion time to get to the careful-driving-requiring area, but the present invention is not always limited to this configuration. Spraying of the spraying device 20 may be cancelled or disabled according to attribute information of the user, information of concentration of the caffeine-containing water solution or the both, which are stored in the memory part 42.

For example, it is commonly known that caffeine intake of pregnant woman does harm for her infant. Thus, the spraying device 20 may refrain from spraying the caffeine-containing water solution 207 when the user selects the option saying that she is pregnant in the third setting field 410c at the initial setting. Here, the information-processing device 40 is configured not to give a spraying-command or to cancel or disable the command. This prevents the spraying device 20 from spraying the caffeine-containing water solution 207.

This framework does not spray the caffeine-containing water solution 207 towards users who should not inhale caffeine, leading to achievement of the safe-driving support system that is user-friendly and healthy for such users.

Additionally, caffeine can make an infant agitated. This fact sometimes means that caffeine intake should be prevented for an infant who needs sleep. Thus, the spraying device 20 may refrain from spraying water solution if the user selects the option that indicates that the company includes an infant in the setting field 410d. Here, the information-processing device 40 is configured not to give a spraying-command or to cancel or disable the spraying-command. This prevents the spraying device 20 from spraying water solution.

This framework prevents spraying the caffeine-containing water solution 207 if the company of the driver includes someone who should not intake caffeine. This contributes to achievement of the safe-driving support system that is user-friendly and healthy for such company as well as the user.

Additionally, a proper amount of caffeine intake per day differs according to such as age and sex. Thus, the spraying device 20 may stop spraying if the whole amount of caffeine sprayed by the spraying device 20 is beyond an upper limit of caffeine intake, which is retrieved from the table of the upper limit of caffeine intake corresponding to the sex inputted in the first setting field 410a and the age inputted in the second setting field 410b. The whole amount of caffeine sprayed is calculatable in a basis of caffeine concentration of the caffeine-containing water solution, which is inputted in the 5th setting field 410e, the amount of spraying of the spraying device per hour, and the duration of the spraying. For example, the upper limit of caffeine intake for a male adult is said to be from 100 mg to 300 mg per day (which may change according to such as weight). From this fact, the upper limit of caffeine intake configured here is 100 mg to be safest. In the embodiment described above, it is assumed that the caffeine concentration of the caffeine-containing water solution is 0.5 mg/ml and the amount of spraying is 50 ml/h. Then, the amount of caffeine sprayed per hour is 25 mg. This means 4 hours is enough to get the upper limit of caffeine intake, 100 mg. Thus, when the caffeine-containing water solution has been sprayed for 4 hours or longer, the spraying device 20 stops spraying even if the user drives for such a long time. Here, the information-processing device 40 is configured not to give a spraying-command or to cancel or disable the command. This prevents the spraying device 20 from spraying water solution.

This framework prevents over-intake of caffeine while awakening the driver or preventing the driver from drowsiness by spraying of the spraying device 20.

2.2 Spraying According to Concentration

In the embodiment described above, the spraying device 20 keeps spraying water solution for certain duration (10 minutes) when the necessary time to get to the careful-driving-requiring area is 15 minute or shorter. However, the present invention does not always have to follow this embodiment. For example, the spraying device 20 may change the duration of spraying or the way of spraying according to the caffeine concentration of the caffeine-containing water solution 207.

The following description is about a variation of spraying with FIG. 8 as reference. In FIG. 8, a course is depicted by solid line. On this course to move along are: the information-processing device 40, which is placed in the car that is moving at the location X toward upper right; and the careful-driving-requiring area A, which may be an accident-prone area. The location A' indicates the point at which the necessary time to get to the area A becomes the criterion time (for example, 15 minutes).

Between A and A' are: the distance between B and B' that is as long as that of A and A; and the distance between C and C' that is shorter than that of B and B'. The starting points (which are point B and point C) and the ending points (which are point B' and point C') are connected to each other by broken lines. The broken line between B and B' indicates the duration of spraying when the caffeine concentration of the caffeine-containing water solution 207 is 0.2 mg/ml (i.e., 15-minute duration of spraying). The broken line between C and C' indicates the duration of spraying when the caffeine concentration of the caffeine-containing water solution is 1.0 mg/ml (i.e., 3-minute duration of spraying). This duration of spraying depends on the caffeine concentration of the caffeine-containing water solution 207. The higher the caffeine concentration of the caffeine-containing water solution 207 is, the shorter the duration of spraying.

This framework prevents over-spraying of the caffeine-containing water solution when the caffeine-containing water solution of caffeine concentration that is so high that the awakening effect and preventive effect of drowsiness is stronger. This therefore prevents waste of the caffeine-containing water solution 207.

In this example, the spray-starting point C, which is for caffeine concentration of 1.0 mg/ml, is located after the point A, but the point C may be at the point A'. Additionally, the spray-ending point C', which is for caffeine concentration of 1.0 mg/ml, may be at the point A.

In this example, the duration of spraying is fixed so that the total amount of caffeine sprayed is fixed. However, the total amount of caffeine sprayed may be unfixed if the higher the caffeine concentration of the caffeine-containing water solution 207 is, the shorter the duration of spraying is.

2.3 Navigation

In the embodiment described above, the application program includes "My drive" mode where the user can confirm the current location of the information-processing device 40 on the map. However, the present invention is not always limited to this embodiment. For example, "My drive" mode may offer navigation as well as the current location on the map.

The information-providing server 60 is connected to bus and comprises a route-searching part 64 that searches the shortest way or the most time-saving way between the current location and the destination after receiving information of the current location and the destination. This route-searching part 64 is not included in figures. When the user inputs his/her destination to the information-processing device 40, the information-providing server 60 provides the shortest way, the most time-saving way or the both in a basis of the result of searching of the route-searching part 64. Following this, the information-processing device 40 starts routing assistance. Here, the information-providing server 60 provides only the careful-driving-requiring area that is in the course of the shortest way or the most time-saving way.

The framework described above enables the user to inhale the caffeine-containing water solution 207, which has the awakening effect or the preventive effect of drowsiness, before the criterion time to get to the careful-driving-requiring area in the course to the destination. This contributes to safe driving. The fixed route prevents waste of spraying and therefore the caffeine-containing water solution 207.

When the user uses the navigating function, the careful-driving-requiring area may include the destination described above. Here, the spraying device 20 may spray water solution before the criterion time so that the user enjoys the awakening effect or the preventive effect of drowsiness at the destination or the area around the destination. This is because a car accident tends to occur in a parking area and because a parking area is commonly the destination of cars. Therefore, the user should enjoy the awakening effect or the preventive effect of drowsiness in such parking areas.

3. Second Embodiment

The first embodiment is a framework where the information-providing server 60 sends the information about the careful-driving-requiring area, including an accident-prone area or a trafficy area. However, it is still possible that the information-providing server 60 somehow fails to precisely store careful-driving-requiring-area information where the user should drive carefully, including a trafficy area. Thus this embodiment describes a framework where the caffeine-containing water solution 207 is sprayed just according to behavior of the information-processing device 40.

The memory part 42 records a history of information about the current location during the present and a certain past time that the GPS unit 44 has obtained periodically. The control part 41 calculates the average velocity during the certain past time by a certain method, including moving average, in a basis of the history of the information about the current location. Then, the control part 41 compares the average velocity calculated with certain reference velocity (for example, 15 kilometer per hour). If the average velocity calculated is equal to or slower than the reference velocity then, the spraying device 20 receives a spraying-command. Upon this reception, the spraying device 20 sprays the caffeine-containing water solution 207 (S208 and S209, as mentioned earlier) as it does in the first embodiment. This means, if the average velocity obtained via GPS is regarded equal to or slower than certain velocity, the car containing the information-processing device 40 is regarded in a traffic jam and the caffeine-containing water solution 207 is sprayed to prevent drowsiness.

The framework described above judges whether the car is in a traffic jam or not in a basis of the information obtained via the GPS unit 44, which is equipped with the information-processing device 40. This enables the spraying device 20 to spray the caffeine-containing water solution that has the awakening effect or the preventive effect of drowsiness. This surely achieves the awakening effect or the preventive effect of drowsiness even if the information-providing server 60 somehow fails to store information about a traffic jam as a careful-driving-requiring area.

INDUSTRIAL AVAILABILITY

The present invention provides the safe-driving support system, which may be applicable to an in-vehicle device.

DESCRIPTION OF SIGNS

10: a car
11: a driver's seat
12: a passenger seat
13a: a drink holder part
13b: a drink holder part
14: a plug for a cigar socket
20: a spraying device
201: a midair cylinder part
202: a body containing a spraying operation part
203: piezoelectric element
204: operation lamp
205: a liquid container
206: a wet retainer
207: caffeine-containing water solution
208: a cut
209: a constricted region
210: power-supply code
21: a control part
22: a memory part
23: a close-range communicator
24: a spraying operation part
40: information-processing device
401: a body
402: a display
403: a control button
404: an in-camera
405: a speaker
406: a time indicator
407: a power indicator
408; a message display
409: a setting item displayed
409a: the first setting item displayed
409b: the second setting item displayed
409c: the third setting item displayed
409d: the fourth setting item displayed
409e: the fifth setting item displayed
410: a setting field
410a: the first setting field
410b: the second setting field
410c: the third setting field
410d: the fourth setting field
410e: the fifth setting field 411: "My drive" mode selection button
412: "Liquid" mode selection button
413: "Store" mode selection button
415: a current-location indicator
416: a warning sign
417: a way where a user is driving
418: a necessary-time-displaying region
419: a caution-displaying region
420: a speed-reminder
421: a time-displaying region
422: a slide-lock displaying region
425: an information notice region
41: a control part
42: a memory part
43: a close-range communicator
44: a GPS unit
45: a radio communicator
60: an information-providing server
61: a control part
62: a memory part
621: a memory part for map data
622: a memory part for careful-driving-requiring areas
63: a communicator
80: a wearable device
801: a main body
802: a displaying part
803a: a control button
803b: a control button
803c: a control button
804: a band
100: a safe-driving support system

The invention claimed is:

1. A safe-driving support system, comprising:
a spraying device having a shape being able to be steadily placed near a driving seat of a movable body and spraying in the movable body;
a mobile information processing device configured to be able to perform proximity communication with the spraying device and being able to obtain current location information via a GPS; and
an information providing server providing the information processing device with information via the Internet; and
the spraying device, further comprising:
a liquid container containing water solution containing caffeine;
a spraying operation part spraying water solution containing caffeine contained in the liquid container; and
wherein the spraying device is configured to spray in the movable body by activating the spraying operation part in response to a spraying command from the information processing device that established proximity communication; and
the information providing server, further comprising:
a map information memory part memorizing map information;
attention requiring area memory part memorizing attention requiring area information showing areas requiring careful driving; and
wherein the information providing server is configured to send the map information and the attention requiring area information, respectively, to the information processing device in response to a request from the information processing device; and
wherein the information processing device obtains the map information and the attention requiring area information from the information providing server by requesting to the information providing server, calculates necessary time to the attention requiring area based upon the map information and the attention requiring area information obtained from the information providing service and the current location information, and generates a spraying command to the spraying device if it is judged that the necessary time is shorter than a criterion time; and
wherein the spraying device activates the spraying operation part based upon the spraying command and sprays the water solution containing caffeine in the movable body.

2. The safe-driving support system as defined in claim 1, further comprising a watch-shaped wearable device being able to perform proximity communication with the information processing device and having a display, and
wherein an image showing spraying is displayed on the display of the wearable device if the information processing device generates the spraying command to the spraying device.

3. The safe-driving support system defined in claim 2, wherein the proximity communication between the spraying device and the information processing device requires a paring process as an initial setting; once the paring process is performed, the proximity communication is automatically established when the spraying device and the information processing device are in a communicable range; and the spraying device sprays immediately after the automatic establishment.

4. The safe-driving support system defined in claim 3, wherein the information processing device is configured to obtain configuration information including attribute information of a user or his or her company, and the spraying device controls spraying water solution containing caffeine according to the configuration information.

5. The safe-driving support system defined in claim 4, the information providing server, further comprising:
a route searching part to search the shortest distance route or the shortest time route between a current location relating to current location information and a destination relating to destination information when the current information and the destination information are provided from the information processing device, and to provide the information processing device with route information relating to the shortest distance route or the shortest time route, and
wherein the information providing server provides the information processing device with attention requiring area information on the shortest distance route or the shortest time route,
wherein the information processing device provides a navigation function based upon the map information and the route information obtained from the information providing server and the current location information, and calculates necessary time to the attention requiring area on the shortest distance route or the shortest time route based upon the map information and the route information obtained from the information providing server, the attention requiring area information on the shortest distance route or the shortest time route and the current location information.

6. The safe-driving support system defined in claim 5, the configuration information, further comprising concentration information of the water solution containing caffeine, and wherein the denser the concentration of the water solution containing caffeine becomes, the shorter the spraying time of the water solution containing caffeine becomes.

7. The safe-driving support system defined in claim 6, wherein the information processing device accumulates spraying amount of the water solution containing caffeine every time the information processing device generates the spraying command, and when the total amount of sprayed water solution containing caffeine calculated based upon the accumulation result and the concentration information is greater than a prescribed value according to the configuration information, the information processing device stops spraying the water solution containing caffeine.

8. The safe-driving support system defined in claim 7, wherein the water solution containing caffeine is odorless.

* * * * *